US009417218B2

(12) United States Patent
Rice et al.

(10) Patent No.: US 9,417,218 B2
(45) Date of Patent: Aug. 16, 2016

(54) DEPLETION OF PLASMA PROTEINS

(75) Inventors: Gregory E. Rice, Warranwood (AU);
Mark S. Baker, Glenwood (AU);
Michael Quinn, Clifton Hill (AU)

(73) Assignee: THERAPEUTICSMD, INC., Boca Raton, FL (US)

( * ) Notice: Subject to any disclaimer, the term of this patent is extended or adjusted under 35 U.S.C. 154(b) by 0 days.

(21) Appl. No.: 12/814,387

(22) Filed: Jun. 11, 2010
(Under 37 CFR 1.47)

(65) Prior Publication Data
US 2011/0008900 A1   Jan. 13, 2011

Related U.S. Application Data

(63) Continuation of application No. 11/983,203, filed on Nov. 6, 2007, now abandoned, which is a continuation of application No. 11/685,176, filed on Mar. 12, 2007, now abandoned, which is a continuation of application No. 10/525,596, filed as application No. PCT/AU03/01075 on Aug. 22, 2003, now abandoned.

(51) Int. Cl.
| G01N 33/543 | (2006.01) |
|---|---|
| G01N 30/14 | (2006.01) |
| C07K 1/22 | (2006.01) |
| G01N 33/68 | (2006.01) |
| G01N 30/00 | (2006.01) |

(52) U.S. Cl.
CPC ........ *G01N 30/14* (2013.01); *C07K 1/22* (2013.01); *G01N 33/6854* (2013.01); *G01N 2030/009* (2013.01)

(58) Field of Classification Search
None
See application file for complete search history.

(56) References Cited

U.S. PATENT DOCUMENTS

| 4,056,737 | A | 11/1977 | Sequin |
|---|---|---|---|
| 4,550,019 | A | 10/1985 | Polson |
| 4,962,189 | A | 10/1990 | Bloch |
| 5,367,054 | A | 11/1994 | Lee |
| 5,420,253 | A | 5/1995 | Emery et al. |
| 6,287,793 | B1 * | 9/2001 | Schenk et al. ............ 435/7.95 |
| 2001/0014468 | A1 * | 8/2001 | Muller-Schulte ......... 435/181 |
| 2001/0051380 | A1 | 12/2001 | Stevens |
| 2002/0082209 | A1 | 6/2002 | Jensenius |
| 2002/0127739 | A1 | 9/2002 | Pieper |

FOREIGN PATENT DOCUMENTS

| DE | 19650991 A1 | 6/1998 | |
|---|---|---|---|
| EP | 0001812 A1 | 5/1979 | |
| EP | 0141939 A2 | 5/1985 | |
| EP | 1540304 B1 | 1/2009 | |
| GB | WO 02/055654 | * 9/2002 | ........... C12M 1/34 |
| JP | 01-123151 A | 5/1989 | |
| JP | 01-175945 A | 7/1989 | |
| WO | WO 99/63351 A2 | 12/1999 | |
| WO | WO 02/055654 A2 | 7/2002 | |
| WO | WO 03/014737 A1 | 2/2003 | |

OTHER PUBLICATIONS

Gassmann et al., Efficient production of chicken egg yolk antibodies against a conserved mammalian protein, FASEB J., 1990, vol. 4, pp. 2528-2532.*
Losso et al., Removal of Bovine Serum Albumin from Cow's Milk using chicken Egg-yolk antibodies immobilized on chitsoan gel, Food and Agricultural Immunology, 1998, 10, pp. 47-56.*
Akita et al., "Isolation of bovine immunoglobulin G subclasses from milk, colostrum, and whey using immobilized egg yolk antibodies," J. Dairy Science, 81: 54-63 (1998).
Allen et al., "Purification of alpha-fetoprotein from human cord serum with demonstration of its antiestrogenic activity," Biochim. et Biophys. Acta, 1202:135-142 (1993).
Baxter, "Circulating levels and molecular distribution of the acid-labile (α) subunit of the high molecular weight insulin-like growth factor-binding protein complex," J. Clin. Endocrinol. Metab., 70:1347-1353 (1990).
Conesa et al., "Determination of IgG levels in bovine bulk milk samples from different regions of Spain," European Food Research and Technology, 220(2)222-225 (2005).
Daly et al., "The search for predictive patterns in ovarian cancer: proteomics meets bioinformatics," Cancer Cell, 1:111-112 (2002).
Davidsson et al., "A new procedure for detecting brain-specific proteins in cerebrospinal fluid," J. Neural. Transm., 104:711-720 (1997).
Decossin et al., "Prevention of in vitro low-density lipoprotein oxidation by an albumin-containing Lp A-I subfraction," Biochim. et Biophys. Acta, 1255:31-38 (1995).
Ding et al., "Human serum LH inhibitor(s): behaviour and contribution to in vitro bioassay of LH using dispersed mouse Leydig cells," Acta Endocrinologica (Copenh), 121:46-54 (1989).
Georgiu et al., "Proteomic analysis of human plasma: failure of centrifugal ultrafiltration to remove albumin and other high molecular weight proteins," Proteomics, 1:1503-1506 (2001).

(Continued)

*Primary Examiner* — Gary W Counts
(74) *Attorney, Agent, or Firm* — Kilpatrick Townsend & Stockton LLP

(57) ABSTRACT

This invention relates to methods of analysis, and in particular to methods for the preliminary fractionation of samples in which low abundance molecules of interest, for example proteins, polysaccharides or fatty acids, are present together with more abundant molecules of little or no interest. In particular, the invention relates to methods of depletion of high abundance proteins from biological samples. Products and kits for use in the method are also disclosed, and form part of the invention. In one aspect, the invention provides a method of depleting a high-abundance molecule from a biological sample, comprising the steps of a) subjecting the sample to affinity depletion using an affinity support with high affinity for a high abundance molecule, and/or b) immunodepletion using an affinity support coupled to an antibody directed against whole or previously fractionated plasma or serum.

15 Claims, 10 Drawing Sheets

(56) References Cited

OTHER PUBLICATIONS

Hage, "Affinity chromatography," Handbook of HPLC, Marcel Dekker, NY, pp. 483-498 (1998).

Hage, "A survey of recent advances in analytical applications of immunoaffinity chromatography," J. Chromatogr., B 715:3-28 (1998).

Hage, "Affinity chromatography: a review of clinical applications," Clin. Chem., 45:593-615 (1999).

Jones, "A review of biotechnology and large scale affinity chromatography," Chromatographia, 32:469-480 (1991).

Kim et al., "Reusability of avidin-biotinylated immunoglobulin Y columns in immunoaffinity chromatography," Anal. Biochem., 268(2):383-97 (1999).

Larsson, "High-performance liquid affinity chromatography," Methods Enzymol., 104:212-223 (1987).

Larsson et al., "Antibody response in laying hens with small amounts of antigen," Food Agri. Immunol., 10(1):29-36 (1998).

Larsson et al., "Chicken IgY: Utilizing the Evolutionary Difference," Comp. Immun. Microbiol. Infect. Dis., 13(4):199-201 (1990).

Little et al., "Clinical and immunological responses in subjects sensitive to solvents," Archives of Environmental Health, 54(1):6-13 (1999).

Lollo et al., "Improved two-dimensional gel electrophoresis representation of serum proteins by using Protoclear™ electrophoresis," Wiley-VCH Verlag, 20(4/5): 854-859 (1999).

Losso et al., "Removal of bovine serium albumin from cow's milk using chicken egg-yolk antibodies immobilized on chitosan gel," Food and Agricult. Immunol., 10(1):47-56 (1998) (Abstract only, XP002223969).

McMartin et al., "Heat treatment of bovine colostrum. I:Effects of temperature on viscosity and immunoglobulin G level," J. dairy Sci., 89(6):2110-2118 (2006).

Onoue et al., "The purification and biological activity of a macrophage-derived factor with interleukin 1-like activities from guinea pigs," Biochim. Biophys. Acta, 881:437-445 (1986).

Pieper et al., "The human serum proteome: display of nearly 3700 chromatographically separated protein spots on two-dimensional electrophoresis gels and identification of 325 distinct proteins," Proteomics, 3:1345-1364 (2003).

Pilch et al., "Large-scale and high-confidence proteomic analysis of human seminal plasma," Genome Biol., 7(5):R40 (2006).

Poutrel et al., "Physiological and pathological factors influencing bocine serum albumin content of milk," J. Dairy Sci., 66(3):535-41 (1983).

Rajic et al., "Protein depletion using IgY from chickens immunized with human protein cocktails," Prep Biochem Biotechnol., 39:221-247 (2009).

Sato et al., "Development of mammalian serum albumin affinity purification media by peptide phage display," Biotechnol. Prog., 18:182-192 (2002).

Scawen, "Dye affinity chromatography," Anal. Proc., 28:143-144 (1991).

Schuchard et al., "Specific depletion of twenty high abundance proteins from human plasma," NCI Proteomics Technologies Reagents Resource Workshop, Dec. 12-13, 2006, retrieved online at http://www.sigmaaldrich.com/etc/medialib/docs/Sigma/General_Information/spec_depletion.Par.001.File.tmp/spec_depletion.pdf on Nov. 11, 2010.

Sharma, "The structure and function of the avian immune system," Acta Veterinaria Hungarica, 45:229-238 (1997) (abstract only, Medline/NLM XP-002395295).

Sorensen, "Isolation of amniotic fluid proteins of non-maternal serum origin by negative immuno-affinity chromatography," Clin. Chim. Acta, 202:199-209 (1991).

Steel et al., "Efficient and specific removal of albumin from human serum samples," Mol. Cell. Proteomics, 2:262-270 (2003).

Yamakawa et al., "Comparative analysis of interindividual variations in the seminal plasma proteome of fertile men with identification of potential markers for azoospermia in infertile patients," J. Androl., 28(6):858-65 (2007).

Conesa et al., "Determination of IgG levels in bovine bulk milk samples from different regions of Spain," Eur. Food Res. Technol., 220:222-225 (2005).

Gassmann et al., "Efficient production of chicken egg yolk antibodies against a conserved mammalian protein," The FASEB Journal, 4:2528-2532 (1990).

Pilch et al., "Large-scale and high-confidence proteomic analysis of human seminal plasma," Genome Biology, vol. 7, Issue 5, Article R40 (2006).

Poutrel et al., Physiological and Pathological Factors Influencing Bovine Serum Albumin Content of Milk, J. Dairy Sci., 66:535-541 (1983).

Rajic et al., Protein Depletion Using IgY from Chickens Immunised with Human Protein Cocktails, Preparative Biochemistry & Biotechnology, 39:221-247 (2009).

Schuchard et al., "Specific Depletion of Twenty High Abundance Proteins from Human Plasma," NCI Proteomic Technologies Reagents Resource Workshop, Dec. 12-13, 2005.

Yamakawa et al., "Comparative Analysis of Interindividual Variations in the Seminal Plasma Proteome of Fertile Men With Identification of Potential Markers for Azoospermia in Interfile Patients," Journal of Andrology, 28(6):858-865 (2007).

* cited by examiner

DEPLETION OF PLASMA PROTEINS

This is a continuation of U.S. Ser. No. 11/983,203, filed Nov. 6, 2007, now abandoned, which is a continuation of U.S. Ser. No. 11/685,176, filed Mar. 12, 2007, now abandoned, which is a continuation of U.S. Ser. No. 10/525,596, filed on Feb. 23, 2005, now abandoned, which is a U.S. national phase application under 35 U.S.C. §371 of International Application No. PCT/AU2003/001075, filed on Aug. 22, 2003, which claims the benefit of Australian Patent Application No. 2002951240, filed on Aug. 23, 2002, the complete disclosures of which are incorporated herein by reference.

This invention relates to methods of analysis, and in particular to methods for the preliminary fractionation of samples in which low abundance molecules of interest, for example proteins, polysaccharides or fatty acids, are present together with more abundant molecules of little or no interest. In particular, the invention relates to methods of depletion of high abundance proteins from biological samples. The method is particularly applicable to samples of human biological fluids such as serum, plasma, tears, saliva, cerebrospinal fluid, uterine washings, amniotic fluid, cervico-vaginal fluid or urine. It is contemplated that the method of the invention will be especially useful for proteomic applications involving biomarker discovery. Products and kits for use in the method are also disclosed, and form part of the invention.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

Following the successful completion of the complete sequence of the human genome in the Human Genome Project, and corresponding successes with other genomes such as the mouse and the rat, there is an urgent need in the art to determine the function of the proteins which these genomes encode, and to determine how these proteins are expressed during various physiological states and in disease.

Proteomics is an area of research which seeks to define the function and relative expression profiles of subsets of proteins encoded by a given genome at a given time in a given cellular location. Proteomics separates, identifies, and characterizes the proteins expressed, retained, secreted or released by a cell or tissue in order to establish their function(s) and their potential relationship to the onset, type, stage and progression of diseases, as well as response to therapy and/or relapse.

Proteomics may be used to compare tissue samples from diseased and healthy people, in order to identify proteins whose expression is changed in disease. Proteins which are significantly altered in their expression, location or post-translational modification (PTM) in patients with a disease, compared to those in a group of healthy individuals, may represent protein targets for drug or discovery of biological markers, for example endpoint and/or surrogate biomarkers. One application of proteomics is in the search for biological markers of disease onset, progression and treatment in elements of the blood, such as serum or plasma.

Serum proteins are useful diagnostic tools, and alteration of the expression of some serum proteins is an early sign of an altered physiology, which may be indicative of disease. In routine diagnostic laboratories, identification of specific low abundant disease-associated proteins in serum relies heavily on time-consuming and expensive radiolabelled or enzyme-linked immunoassay methods (RIA or ELISA) which only have the ability to evaluate a single protein component at a time. Due to the heterogenous nature of most physiological disorders, it is generally considered that no single marker is likely to be sufficiently predictive of disease, so that there is a need for more than one candidate biomarker to enhance already available diagnostic or prognostic tests. It has been suggested that a panel of multiple diagnostic/prognostic markers in serum can be identified by utilizing proteomic approaches which have the capacity to profile multiple biomarkers (Daly and Ozols, 2002).

One primary tool used in proteomic methods for protein separation and analysis of proteins is two-dimensional gel electrophoresis (2DE). Following separation by 2DE, proteins are characterized and identified, usually using matrix-assisted laser desorption interferometery (MALDI) peptide mass fingerprinting or other forms of advanced mass spectrometry, for example, electrospray mass spectroscopy (MS) or time-of-flight (TOF)/TOF MS, or surface-enhanced (SELDI-TOF MS), laser desorption ionization time-of-flight mass spectrometry coupled to protein and genomic database searching.

Unfortunately, the analysis by 2DE gels of proteins in samples of biological fluids such as serum and plasma is very difficult. This is because of the limited amount of protein able to be resolved by a gel, and the great variation in the concentration of proteins in many samples. This variation in concentration is frequently referred to as "dynamic range". These factors result in data obtained by 2DE from complex samples, such as unfractionated serum and plasma, being dominated by the presence of proteins which are of high abundance in blood, for example human serum albumin, immunoglobulin G (IgG), haptoglobin, fibrinogen, transferrin, $\alpha_1$-antitrypsin, $\alpha_2$-macroglobulin, IgA, and IgM. Of these, six (albumin, IgG, IgA, $\alpha_1$-antitrypsin, transferrin and haptoglobin) constitute 85-90% of the protein mass in blood serum. Proteins with a concentration higher than 1 mg/mL are generally considered to be of high abundance, and such proteins may represent 2-60% of the total protein present.

Thus the application of current proteomic technologies is limited by the presence of high abundance "housekeeping" proteins like albumin and immunoglobulins, which constitute approximately 60-97% of the total serum protein (Georgiou et al, 2001). Such proteins hinder the detection of hundreds of low abundance proteins, some of which might potentially be relevant to a particular disease state. Moreover, the widely spread pattern of albumin and immunoglobulin in the 2-DE gel can also obscure proteins with a similar pI and molecular weight. Theoretically, by removing albumin and immunoglobulin, which together constitute 60-97% of the total serum protein, 3-5-fold more protein can be analyzed. If proteomic technologies are to be used routinely for diagnostic purposes, a rapid, inexpensive and simple method is required to remove the high abundant proteins.

In particular, the presence of these abundant proteins severely limits the utility of methods used in wide scale analysis of proteins present in complex mixtures of proteins, such as single dimension electrophoresis (IDE), 2DE, multi-dimensional liquid chromatography and MS. These methods are often used in the investigation of low-abundance proteins such as cytokines, signal transduction proteins, hormonal mediators, and cancer biomarkers. The dynamic range problem is illustrated in FIG. 1, which shows the results of 2DE of a sample of unfractionated human plasma. This illustrates the problem presented by very abundant proteins, such as albumin, which comprises more than 80% of the total protein present in plasma; see the circle in FIG. 1. As the total amount of protein which can be loaded on to a gel is limited to less than approximately 120 mg, the maximum amount of "non-albumin" proteins which can be loaded is limited to approximately 36 mg, thus limiting the ability of this technique to visualize and identify putative clinically-relevant low abundance biomarker proteins. Rare proteins may be difficult if not impossible to detect. Similar, although less extreme, dynamic range problems are experienced with 2DE analyses of other types of biological samples, such as urine, tissue extracts, and cell lysates.

One approach to solving this problem is to develop methods for removing albumin and other highly abundant proteins from blood samples such as serum and plasma before analysis, thus increasing the sensitivity of the analysis and hence the likelihood of identifying low abundance protein biological markers. In particular, a method of removal of the 50 to 100 most abundant proteins from plasma before analysis would be greatly advantageous, in order to permit the use of higher relative mass loading of samples.

SUMMARY OF THE INVENTION

We have now surprisingly found that a simple immunoaffinity procedure, combined with the use of existing solid phase affinity capture supports, can be used to rapidly remove high abundance proteins from biological samples, giving a dramatic improvement in the separation of low-abundance proteins by 2DE.

It is to be clearly understood that while the invention is specifically illustrated with reference to proteins, a similar procedure may be used to separate any low-abundance molecule from a complex sample. In addition to low-abundance proteins, the procedure may also be used to separate low-abundance polysaccharides or fatty acids from a complex sample.

In a first aspect, the invention provides a method of depleting a high-abundance protein molecule from a biological sample, comprising the steps of a) subjecting the sample to affinity depletion using an affinity support with high affinity for a high abundance molecule, and/or b) immunodepletion using an affinity support coupled to an antibody directed against whole or previously fractionated plasma or serum, in which the antibody binds to a high abundance molecule.

Preferably the sample is subjected to both affinity depletion and immunodepletion. While it is possible to perform the steps in either order, we have found that by performing step (a) before step (b) much less antibody is required for substantially complete removal of high abundance molecules. Therefore this order is preferred.

Preferably the high abundance molecule is a protein. Even more preferably, the protein is albumin. Preferably the antibody is an avian antibody.

Preferably the biological sample is a biological fluid, such as serum, plasma, lymph, cerebrospinal fluid, amniotic fluid, cervicovaginal fluid, uterine fluid, or seminal fluid. Alternatively the sample may be conditioned medium from a cell or tissue culture, or may be a tissue or cell extract, especially an extract of a highly vascularized tissue.

The biological sample may be obtained from any mammalian species, including humans, companion animals such as dogs and cats, domestic animals such as horses, cattle and sheep, or zoo animals such as non-human primates, felids, canids, bovids, and ungulates. Preferably the sample is obtained from a human.

The mammal may be of either sex, may be of any age, and may be either healthy or suffering from any kind of pathological condition, including but not limited to infections, cancers, or chronic degenerative conditions. In other words, the method of the invention is applicable to any situation where it is desired to perform analysis in order to detect a low abundance molecule, or to identify whether there is a change in the pattern of expression of such a molecule in a mammal.

The affinity support used in step (a) may be any such support which is known to have a high affinity for albumins, immunoglobulins or other highly abundant proteins. Typically the support will be a dye affinity chromatography resin, in which a solid support is coupled to a dye such as a chlorotriazine compound, including but not limited to Cibacron blue F3GA affinity supports such as Affi-Gel® Blue (Bio-Rad Laboratories), a bifunctional affinity/ion exchange chromatography matrix, or Blue Sepharose® (Amersham Biosciences), a crosslinked, beaded-form of agarose. Other dye-ligands which could also alternatively be employed to remove abundant blood proteins include Procion Red HE3B, Reactive Blue MRB, Reactive Green H4G, Reactive Green HE4BD, Reactive Green HE4BD, Reactive Yellow M8G, and Reactive Brown M4R, all of which can be coupled to supports such as Sepharose® 4B and 6B. Dyes suitable for use in affinity chromatography are discussed in a review by Scawen (1991). Alternatively the support may be coupled to a protein such as Protein A, Protein G or Protein A/G fusions. Affinity chromatography techniques are well known in the art, and are reviewed in Hage (1999) and Larsson (1987).

The affinity depletion in step (a) may involve the use of magnetic beads such as agarose (Dynabead M-280) as a solid phase matrix support for an affinity ligand for the magnetic separation of high abundance molecules from low abundance molecules.

Similarly, any solid-phase support which can be coupled to an immunoglobulin to form an affinity support may be used in step (b); these include but are not limited to agarose gels such as Sepharose® 4B or Sepharose® 6B (Pharmacia), cross-linked agarose, or acrylamide-based and cellulose-based beads.

The antibody used in step (b) may be a first generation polyclonal antibody raised against whole serum or plasma, or against any fraction of these complex proteinaceous mixtures, and may suitably be raised using an immunization schedule comprising multiple booster injections. The antibody may be raised in any convenient avian or mammalian species. Where the antibody is an avian antibody, this may be raised in any convenient species of bird, but most conveniently will be raised in a poultry species such as a chicken, turkey, duck or goose. Most preferably the avian antibody is a chicken antibody. In one embodiment the antibody is chicken IgY. The high-abundance molecule may be conjugated to a carrier protein if necessary in order to increase immunogenicity.

More preferably the antibody is a second generation polyclonal antibody raised against plasma or serum which has already been subjected to at least one round of affinity depletion and immunodepletion IgY directed against homologous plasma or serum. The antibody may be produced and purified using any conventional method. Suitable methods for preparation of IgY are disclosed in U.S. Pat. No. 5,367,054, U.S. Pat. No. 5,420,253, U.S. Pat. No. 4,550,019 and U.S. Pat. No. 4,056,737.

It is also to be clearly understood that the procedure may be performed prior to any separation technology. Suitable separation technologies include, but are not limited to, one-dimensional gel electrophoresis (1DE), 2DE, capillary electrophoresis, mass spectrometry, high-pressure liquid chromatography (HPLC), gas-chromatography, liquid chromatography (LC), multi-dimensional LC, or LC/MS.

Thus in a second aspect, the invention provides a method of separation or analysis of a low abundance molecule in a biological sample, comprising the step of depleting a high abundance molecule from the sample by the method of the first aspect of the invention, and then subjecting the thus-treated sample to a separation method, such as chromatography, electrophoresis or mass spectrometry. The separation methods described above are preferred.

In a third aspect, the invention provides a composition for immunodepletion of a high abundance molecule from a biological sample, comprising an antibody preparation directed against a high abundance molecule, coupled to an affinity support. Preferably the antibody is an avian polyclonal antibody, more preferably a second generation avian polyclonal antibody, and the high abundance molecules are those present in serum or plasma. Even more preferably the avian antibody is from chicken, and the serum or plasma molecules are serum or plasma proteins. In one embodiment the antibody is chicken IgY.

As in step (b) of the first aspect of the invention, the support may be any solid-phase support which may be coupled to immunoglobulin to form an affinity support. Many suitable supports are known in the art, such as Sepharose® and the like, as described above.

In a fourth aspect, the invention provides a device for the rapid processing of biological samples in the method of the invention, comprising a generally cylindrical chamber having an opening at either end, in which each opening is adapted to fit sealingly to a receptacle, in which the sample can be transferred from one receptacle to the other via the chamber, and in which the chamber has transversely disposed within it multiple layers of an affinity support having a high affinity for high abundance molecule, separated by a layer of an affinity support coupled to one or more antibodies directed against a high abundance molecule.

Preferably the high abundance molecule(s) is/are albumin and/or immunoglobulins, the antibody is avian, and the abundant molecule(s) is/are plasma or serum proteins.

The term "sealingly" means that the chamber fits to the receptacle sufficiently tightly that substantially no fluid can escape when fluid is passed from one receptacle to another via the chamber. The plane of each layer of the support is generally perpendicular to the axis of the chamber. In use, the chamber is connected at one end to a receptacle containing a fluid, biological sample, and at the other end to an empty receptacle, and the sample is passed a number of times from one receptacle to the other through the chamber.

In one embodiment the receptacles are hypodermic syringes and the chamber is a Luer-type cartridge. More preferably both the chamber and the receptacles are made of plastics. In a second embodiment the chamber is adapted to be coupled directly to a separation or analytical apparatus such as an HPLC or LC column, or a mass spectrometry. For example, a Sep-Pale type cartridge would be suitable.

In a fifth aspect, the invention provides a kit for removal of high-abundance molecules from a biological sample, comprising:

a) a first affinity support with high affinity for high abundance molecules, such as albumin and/or other highly abundant proteins such as IgG; and b) a second affinity support coupled to an antibody directed against whole or previously fractionated serum or plasma, in which the antibody binds to a high abundance molecule.

Preferably the antibody is an avian antibody, and is directed against the whole serum or whole plasma, or against high abundance serum or plasma proteins.

Preferably the kit also comprises a device according to the fourth aspect of the invention; optionally the kit may also comprise a diluent suitable for use with biological fluids.

In both the fourth and the fifth aspects of the invention the affinity supports are as described for the first aspect.

BRIEF DESCRIPTION OF THE FIGURES

FIG. 4 shows the results of 2DE of a sample of human plasma subjected to 4-7 IPG isoelectric focusing and 10% acrylamide SDS-PAGE (Criterion gel Bio-Rad), and visualized by SYPRO Ruby®.

DETAILED DESCRIPTION OF THE INVENTION

Figure 1:
FIG. 1 shows the results of 2DE of a sample of human plasma. The circle indicates spots representing albumin.

It is to be clearly understood that this invention is not limited to the particular materials and methods described herein, as these may vary. It is also to be understood that the terminology used herein is for the purpose of describing particular embodiments only, and it is not intended to limit the scope of the present invention, which will be limited only by the appended claims.

As used herein, the singular forms "a", "an", and "the" include the corresponding plural reference unless the context clearly dictates otherwise. Thus, for example, a reference to "a protein" includes a plurality of such proteins, and a reference to "a molecule" is a reference to one or more molecules. Unless defined otherwise, all technical and scientific terms used herein have the same meaning as commonly understood by one of ordinary skill in the art to which this invention belongs. Although any materials and methods similar or equivalent to those described herein can be used to practice or test the present invention, the preferred materials and methods are now described.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

For the purposes of this specification, the term "Affinity depletion" means the removal of components from a complex mixture based upon chemical or immunological characteristics by specific agents.

The term "Affinity support" refers to a matrix or support to which specific agents are bound or coupled and which is used to deplete components from a complex mixture.

"Immunodepletion" means the use of antibodies raised against specific components of a complex mixture to remove those components from the mixture.

"Immunoaffinity" refers to the association between an antibody and its corresponding antigen or epitope.

"High affinity" refers to the strength of binding between an antibody and its corresponding antigen or epitope, and the person skilled in the art will readily be able to determine whether a given antibody binds strongly enough to a high abundance protein to be useful for the purposes of the invention. In general secondary antibodies have higher affinity than primary antibodies, so antibodies elicited by a series of two or more immunizations will be expected to have higher affinity than those obtained after a single immunization.

The terms "high abundance protein", "high abundance molecule", or "highly abundant protein" refer to a protein which is present at a concentration greater than 1 mg/ml in a biological sample.

Abbreviations used herein are as follows
AHP anti-human plasma antibody
BPB bromophenol blue
CHAPS 3-[(3-cholamidopropyl)-dimethylamino]-2-hydroxyl-1-propane
DTT dithiothreitol
EDTA ethylene diamine tetraacetic acid
IgY immunoglobulin Y
PEG polyethyleneglycol
TBP tributylphosphine
2DE two-dimensional electrophoresis In a preferred embodiment of the invention, we have found that depletion of albumin using a Cibacron Blue-based affinity support greatly reduces the number of protein spots detectable by SYPRO Ruby® staining of 2DE gels. Using this step in conjunction with a second step of immunodepletion with an immuno-affinity support coupled to an IgY further reduces the number of spots, as well as enabling the detection of previously undetectable spots.

The avian equivalent of IgG, usually referred to as IgY, is significantly different in its chemical and physical properties from IgG. In particular, in addition to having different amino acid composition and sequence, IgY has a much higher electrophoretic mobility, a much lower isoelectric pH, and a higher molecular weight than IgG, and has substantially different chemical stability. Under certain conditions IgY requires stabilization by non-ionic surfactants, whereas IgG is stable in the absence of surfactants. Ionic detergents can inhibit the reaction of IgG with some antigens, but these agents have little effect on the ability of IgY to bind antigens. IgY is monomeric in 0.15 M NaCl (low salt conditions), and is dimeric in 1.5 M NaCl (high salt conditions), while IgG is monomeric at both low and high salt conditions. The properties of IgY are described in detail in U.S. Pat. No. 4,550,019. The structural differences between the two molecules mean that the hinge region which is present in IgG between the Fab pieces is absent in IgY. This hinge region renders IgG less stable than IgY, and hence IgG is slightly less suitable than IgY for use in solid-phase extraction procedures.

The yolk of eggs laid by immunized chickens is an abundant source of polyclonal antibodies (pAb). Specific antibodies produced in chickens offer several important advantages over producing antibodies in other mammals, such as those mentioned above.

Due to the phylogenetic distance between birds and mammals, there is greater probability of producing a higher percentage of specific antibody against mammalian antigens by immunizing chickens than by immunizing other animals. Highly conserved mammalian proteins sometimes fail to elicit a humoral immune response in animals, such as rabbits, which are traditionally used for generating polyclonal antibody. Since chicken IgY does not cross-react with mammalian IgG, and does not bind bacterial or mammalian Fc receptors, non-specific binding is reduced, and the need for cross-species immunoabsorptions is also eliminated.

Two affinity supports were used in the pre-fractionation of serum or plasma prior to 2DE and the consequent display of the low abundance proteome. Affil-Gel® Blue has been previously used to remove albumin and certain other proteins from serum samples. However, to our knowledge it has not hitherto been suggested that Affi-Gel® Blue could be useful in preparation of samples for 2DE analysis. Affi-Gel® Blue and similar supports, such as HiTrap™ Blue P (Amersham Biosciences) desalting columns, are agarose supports coupled to the dye Cibacron Blue F3G-A, which has a high affinity not only for albumin, but also for interferon, a broad range of nucleotide-requiring enzymes, $\alpha_2$-macroglobulin, coagulation factors, and nucleic acid-binding proteins. Thus it depletes not only albumin but also $\alpha_2$-macroglobulin and coagulation factors from plasma.

A variety of ligands based on synthetic dyes, such as triazine or triphenylmethane compounds, are used in a technique known as "dye-ligand affinity chromatography". Specific ligands used in this method include Cibacron Blue F3G-A, Procion Blue MX-3G or MX-R, Procion Red HE-3B, and Thymol Blue or Phenol Red (Hage, 1998; Hermanson et al, 1992). Although these compounds are all synthetic rather than naturally-occurring, they are classified as affinity ligands because they interact with and bind to many biomolecules such as proteins and enzymes by mimicking the structure of their substrates, cofactors, or binding agents. For example, Cibacron Blue F3G-A consists of a chlorotriazine ring which has several substituents, one of which is an anthraquinone which interacts with enzymes which have a binding site for NAD+, NADP+, or ATP.

These dye ligands can be produced in large quantities and demonstrate a high degree of selectivity and reproducibility. These properties have made them useful for the large-scale purification of dehydrogenases, kinases, albumin, α-fetoprotein, CoA-dependent enzymes, hydrolases, IgG, lipoproteins, nucleases, polymerases, synthetases, and transferases (Hage, 1998; Hermanson et al, 1992; Jones, 1991; Scawen, 1991).

The invention will now be described in detail by way of reference only to the following non-limiting examples and drawings.

EXAMPLE 1

Production of Polyclonal Antibodies to Human Plasma

Figure 2:
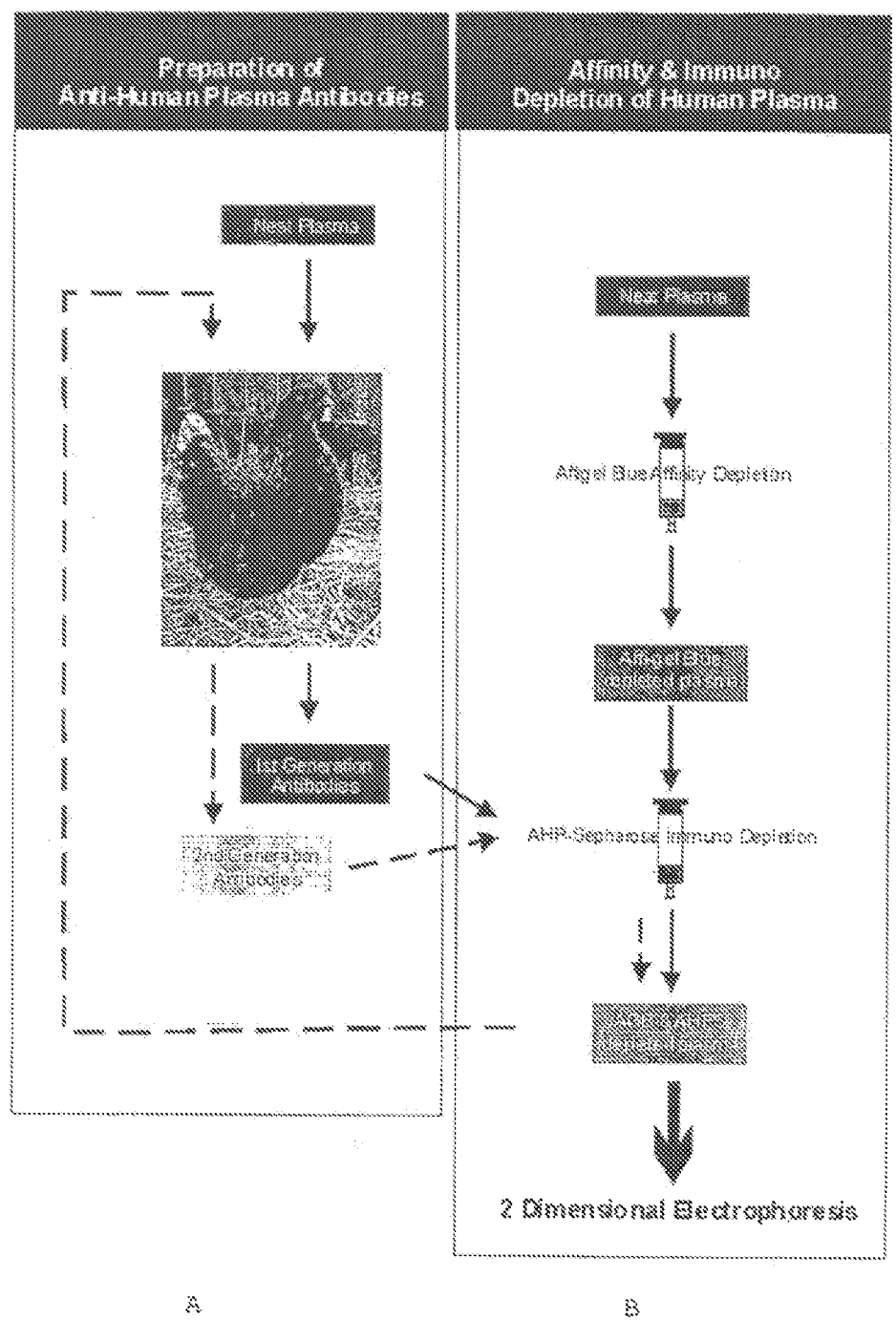
FIG. 2A is a schematic illustration of the process for production of first and second generation polyclonal antibodies in chickens.
FIG. 2B is a schematic illustration of the processes for affinity and immunodepletion of proteins from human plasma.
Figure 3:
FIG. 3 is a Western blot of a 2DE of a sample of whole human plasma. The blot was probed with pooled first and second round chicken antibody raised against human plasma, and demonstrates the range of abundant protein antigens against which antibody responses have been mounted by the immunised chickens.

First generation polyclonal antibodies to human plasma were produced in female chickens. The procedure is summarised in FIG. 2. Chickens (14 week old White Leghorn/Rhode Island Red cross) were immunised according to the recommendations of the 21$^{st}$ European Centre for the Validation of Alternative Methods (ECVAM) workshop, using 1 mg plasma proteins/bird (12.5 µl of 80 mg/ml) suspended in saline (87.5 µl)/Freund's Incomplete Adjuvant (100 µl). 100 µl of total plasma proteins were injected subcutaneously over the pectoralis major muscle, using a 25-gauge needle at four sites (i.e. 50 µl per site).

Birds received three booster injections as described above, 4, 8 and 12 weeks later. Eggs were collected prior to immunization and the yolks stored at −20° C. Eggs were collected daily during the immunization schedule, up to 30 days after the last booster injection and the yolks extracted as described in Example 2.

EXAMPLE 2

Extraction of IgY

Egg yolks (10 per batch) were separated and then suspended in 2 volumes of 100 mM phosphate buffer (pH7.6) in a glass beaker. An equal volume of chloroform was added and then stirred for 5 min at room temperature. The resultant emulsion was then transferred to 100 ml glass centrifuge tubes and centrifuged at 2000 g for 1 h at 4° C. The supernatant was collected and its volume determined. PEG 6000 (Sigma Chemical Company, St Louis, USA) was dissolved in the supernatant to final concentration of 12% w/v, incubated for 10 min at room temperature and then centrifuged at 2000 g for 1 h at 4° C. The supernatant was discarded and the pellet resuspended in 100 mM phosphate buffer pH7.6 (⅙ original yolk volume) and stored at −20° C. as 1 ml aliquots.

Egg yolks were collected for four weeks following the final immunization, pooled and extracted as described above.

The binding characteristics of the extracted antibodies were determined by 2DE Western Blot analysis as described below. The antibodies were then coupled to Sepharose® 4B according to the manufacturer's instructions.

EXAMPLE 3

Coupling of IgY to Sepharose® 4B

PEG 6000 was dissolved in 2 ml IgY solution (17.3 mg protein/ml), incubated for 10 min at room temperature and then centrifuged at 2000 g for 1 h. The pellet was resuspended in coupling buffer (0.1M NaHCO$_3$ pH 8.3, containing 0.5M NaCl) to a final concentration of 7.5 mg protein/ml.

CNBr-activated Sepharose® 4B (Pharmacia; 1 g) was suspended in 20 ml of 1 mM HCl. The suspension was then washed with 200 ml 1 mM HCl on a sintered glass filter. The washed gel was resuspended in the IgY solution, and mixed on a rotary mixer for 18 h at 4° C. The gel was then washed with 5 volumes of coupling buffer and incubated in 0.1M Tris-HCl buffer, pH8.0 for 2 h at 4° C. The gel was washed 3 times alternately with 5 volumes 0.1M acetate buffer pH 4.0 containing 0.5M NaCl, and then 0.1M Tris HCl pH 8.0 containing 0.5M NaCl. The anti-human plasma antibody-Sepharose® 4B (AHP-Sepharose®) gel was then stored at 4° C. in 0.01 M phosphate-buffered saline, PH7.4, containing 0.05% sodium azide as a preservative.

EXAMPLE 4

Preparation of Affinity-Depleted and Immunodepleted Plasma

Plasma from normal human males was subjected to affinity depletion using Affi-Gel® Blue and immunodepletion using AHP-Sepharose®. Affi-Gel® Blue (5 ml gel suspension per ml of plasma) was suspended in sealed 10 ml polypropylene columns (Econo-Columns; Bio-Rad) and eluted with 2 volumes of 20 mM phosphate buffer (pH7.1). Plasma (500 µl) was mixed with an equal volume of 20 mM phosphate buffer (pH7.1) and mixed on a rotary mixer for 4 h at 4° C. ml. This solution was then added to the Affi-Gel® Blue column. The column was capped and mixed on a rotary mixer for 18 h at 4° C. The column tip seal and cap were removed, and the flow-through collected. The protein content was determined, and the aliquot was stored at −80° C. for subsequent analysis.

The residual Affi-Gel® Blue-treated plasma was then subjected to AHP-Sepharose® immunodepletion as follows. AHP-Sepharose® (100 µl) was washed with 4 volumes of 100 mM phosphate buffer (pH7.1) using a sintered glass filter. The washed gel was resuspended in Affi-Gel® Blue-treated plasma (100 µl) in a 2 ml microcentrifuge tube, and mixed on a rotary mixer for 18 h at 4° C. The suspension was centrifuged at 13,200 g for 5 min at room temperature and the supernatant collected, its protein content determined and the aliquot then stored at −80° C. for subsequent analysis.

Affinity-depleted and immunodepleted plasma was then used as antigen to raise second-generation antibodies in chickens, using the same immunization schedule as in Example 1. The antibodies raised were evaluated individually and pooled for evaluation of their effects on the removal of proteins from untreated and Affi-Gel® Blue-treated plasma respectively. The process of antibody preparation is summarised in FIG. 2.

EXAMPLE 5

Removal of High Abundance Proteins from Human Serum Samples

Human serum samples were treated with Affi-Gel® Blue by the following process for the primary removal of albumin. For serum samples, whole blood (2 ml) was collected by venepuncture into plain collection tubes, in which blood was allowed to clot at room temperature for 30 min and then processed. Samples were then centrifuged at 2000 g for 10 min, after which serum was collected. For plasma samples, whole blood was collected in the same way into EDTA anticoagulant tubes. An aliquot (100 µl) was removed for the determination of total protein. Serum and plasma samples were stored at −80° C. until analysed.

Samples were thawed at room temperature and incubated with 5 volumes of Affi-Gel® Blue for 16 h at 4° C. room on a rotary platform. Samples were then centrifuged at 2000 g for 10 min. The supernatant was recovered, an aliquot (100 µl) was removed for the determination of total protein and 2DE analysis, and the remainder of the sample was incubated with either first or second generation anti-human plasma antibody coupled to Sepharose® 4B for 4 h at 4° C. The samples were then centrifuged for 20 min at 2000 g at 4° C. The supernatant was recovered, an aliquot (50 µl) was removed for determination of total protein, and the remainder stored at −80° C. until subjected to 2DE analysis.

EXAMPLE 6

Two-Dimensional Electrophoresis

First Dimension Separation

2 µl serum diluted in 48 µl of sample preparation buffer (62.5 mM Tris HCl, 2% SDS, 25% glycerol, 0.01% bromophenol blue and 2.3% DTT, pH 7.8), and incubated at 95° C. for 5 min. 15 µg (~7 µl) of serum protein was mixed with solubilization buffer for isoelectric focusing (7M urea, 2M thiourea, 100 mM DTT, 4% CHAPS, 0.5% carrier ampholytes pH4-7, 0.01% BPB and 40 mM Tris) to a final volume of 200 µl and incubated for 1 h at room temperature. This mixture was then applied to a ReadyStrip™ (11 cm, pH 4-7, Bio-Rad), which consist of dehydrated polyacrylamide gels cast on solid film, and actively rehydrated at 50V and 20° C. for 16 h. Serum proteins were isoelectrically focused at 250V for 15 min and then 8000V for 150 min, and then maintained at 8000V for a total of 35000 Vh/gel, i.e. a total of 42000 Vh per gel. Ready Strips were then stored at −80° C. until second dimension processing.

Second Dimension Separation

Ready Strips from the first dimension separation were equilibrated in 6 ml of equilibration buffer (50 mM Tris-HCl pH 8.8, 6M urea, 30% glycerol, 2% SDS, 0.01% BPB, 5 mM TBP). Strips were rinsed in Tris-glycine SDS running buffer (25 mM Tris, 192 mM glycine, 0.1% w/v SDS, pH 8.3) and then applied to the top of a Ready Gel (10% or 8-16% acrylamide, Criterion Gel; Bio-Rad). Low melting point agarose (0.5% in running buffer containing BPB) was layered on top of the strip. Two wicks to which molecular weight markers were applied were inserted into the agarose. Gels were electrophoresed at 10 mA/gel for 1 hr, 20 mA/gel for 2 h and then at 30 mA/gel for 30 min. Gels were fixed in methanol/acetic acid (40%/10% in deionised MilliQ water for 1 h at room temperature and then incubated in Sypro Ruby® (Bio-Rad) for 16 h at room temperature on a rocking platform. Gels were destained for 1 h in methanol/acetic acid (10%/7% in dH$_2$O). The gels were imaged using a Bio-Rad FX imager at 100 nM resolution.

Figure 4A:
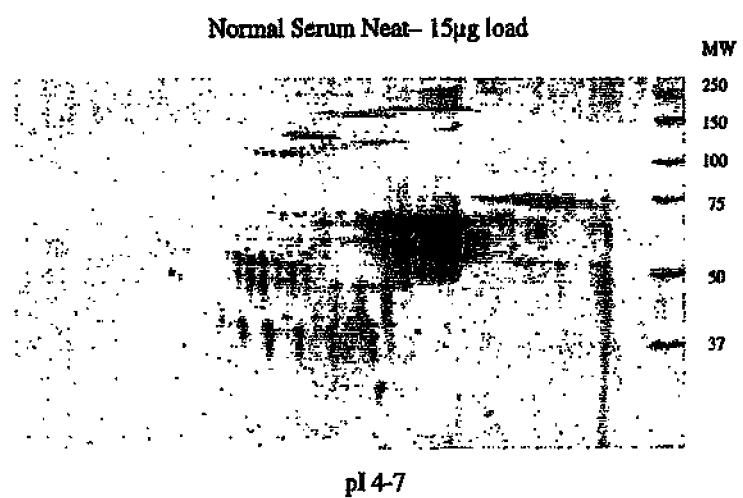
FIG. 4A is a display of proteins present in unfractionated human plasma.
Figure 4B:
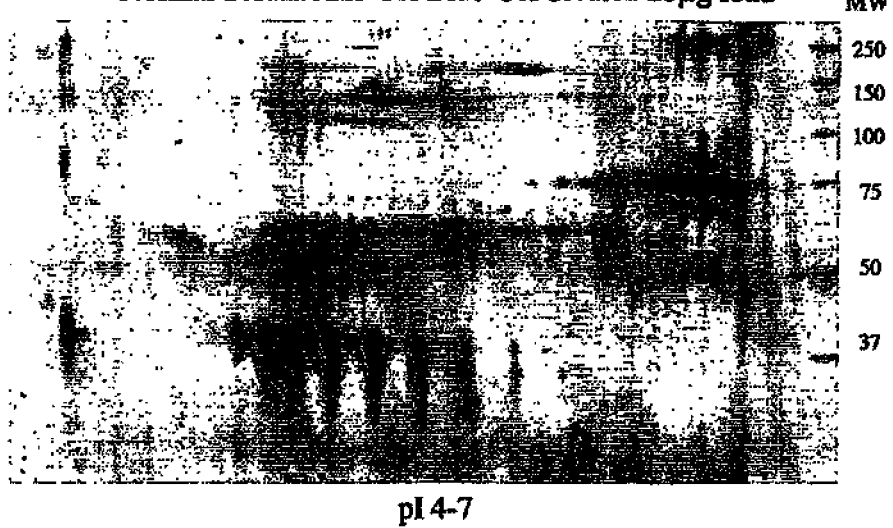
FIG. 4B is a display of proteins present after treatment of human plasma with Affi-Gel® Blue.
Figure 4C:
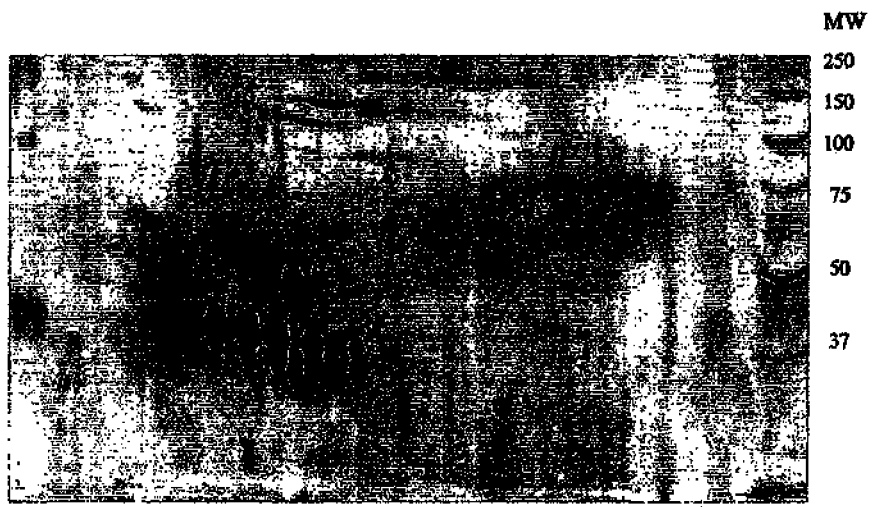
FIG. 4C is a display of proteins present after treatment of human plasma with Affi-Gel® blue and then anti-human plasma (AHP)-Sepharose® 4B.
Figure 5:
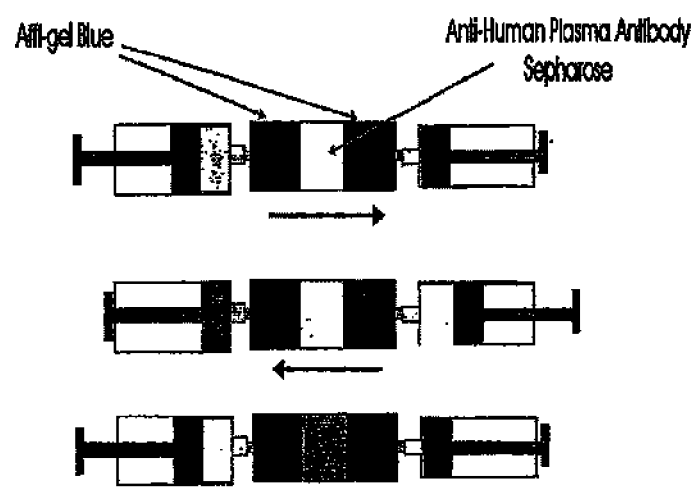
FIG. 5 is a schematic representation of a cartridge device according to the invention for rapid processing of samples of biological fluids.

FIG. 4 shows a comparison between the number of protein species identifiable by 2DE which can be detected using pooled a) first and second round anti-human plasma chicken antiserum in control, untreated human plasma, b) plasma subjected to plasma subjected to affinity depletion and immunodepletion using first generation polyclonal antibody, and c) plasma subjected to affinity depletion and immunodepletion using second generation polyclonal antibody.

The analysis of the protein spots in FIG. 4 is summarised in Table 1. This shows that the method of this invention leads to the removal of the majority of the protein spots present in undiluted, untreated control plasma (neat plasma), while revealing a very high proportion of previously undetected proteins.

TABLE 1

Comparison of protein spots identified by image analysis of 2DE display of untreated serum (neat), serum treated with Affi-Gel ® blue (AGB) and serum treated with AHP-Sepharose ®.

| PROTEIN SPOT COMPARISION | neat (untreated) | AGB Treated | AHP Sepharose ® Treated |
|---|---|---|---|
| Total number of protein spots displayed | 248 | 152 | 157 |
| Number of spots common to both neat and post-treatment protein displays | NA | 127 | 130 |
| Number of spots identified only after treatment | NA | 25 | 27 |
| Number of protein spots increased by 5-fold or greater following treatment compared to neat | NA | 9 | 9 |
| Number of protein spots decreased by 5-fold or greater following treatment compared to neat | NA | 28 | 16 |
| Spot unique to specific treatment (AGB vs AHP) | NA | 14 | 15 |
| Number of protein spots that were ≥2-fold greater in AGB than AHP Sepharose ® | NA | 12 | — |
| Number of protein spots that were <2-fold less in AGB than AHP Sepharoses ® | NA | 20 | — |

NA: not applicable

EXAMPLE 7

Device for Rapid Sample Processing

Figure 6:
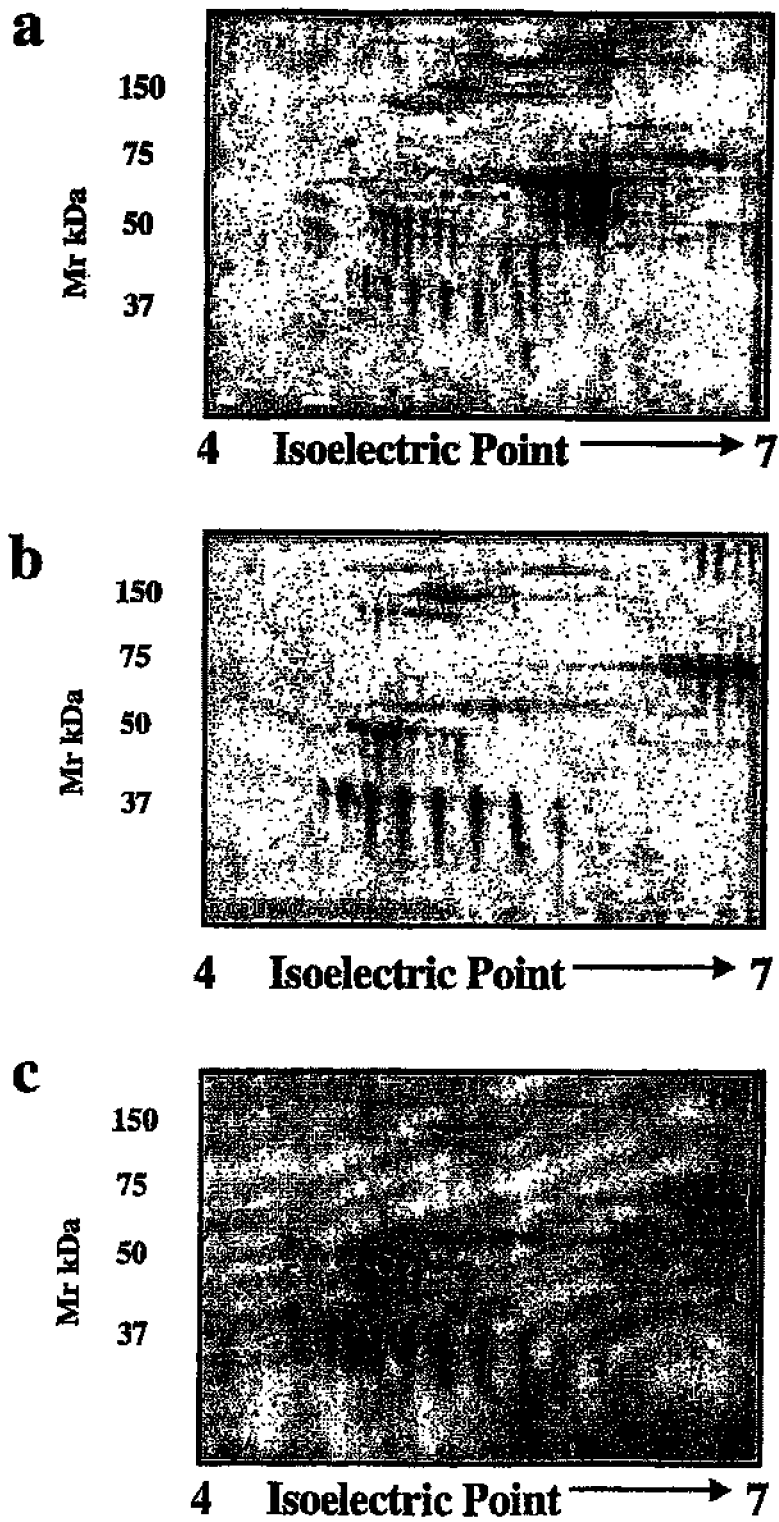
FIG. 6 is a 2-DE profile of (a) Untreated serum, (b) Affi-Gel® Blue and (c) Aurum™, an RNA extraction kit-treated human serum. Human serum was treated with Affi-Gel® Blue or Aurum™ kit for 16 h before analysis by 2-DE. 15 µg of protein was loaded on each gel. Results are representative of three independent experiments.

The process and product of the invention for the preparation of either serum or plasma samples for the display of a low abundance proteome may be used in the form of a sealed Luer-type cartridge suitable for use together with plastic syringes. Anti-human plasma antibody resin (0.5 ml) is sandwiched between two bands (0.5 ml each) of Affi-Gel® Blue resin, or other protein-binding resin, in a 1.5 ml cartridge. A 2.5 ml syringe containing 1 ml of serum is connected to one end of the cartridge, and an empty 2.5 ml syringe is connected to the other end of the cartridge. This device is illustrated in FIG. 6. The serum sample is refluxed through the cartridge 5 times, and then collected and stored for 2DE analysis. The cartridge and syringe may be provided as a kit.

EXAMPLE 8

Comparison of Depletion with Affi-Gel® Blue or Protein A

Samples of normal human serum were subjected to affinity depletion with either Affi-Gel® Blue or Affigel-Protein A plus Affi-Gel® Blue prior to 2DE analysis.

Human blood was collected from healthy volunteers (n=6) at the Royal Women's Hospital, Melbourne, after the provision of a participant information statement and with informed consent. Whole blood (10 ml) was collected by venepuncture into plain collection tubes for serum (blood was allowed to clot at room temperature for 30 min). Samples were centrifuged at 2000 g for 10 min after which serum was collected. An aliquot (100 µl) was removed for the determination of total protein. Serum was stored at −80° C. until analyzed.

Total protein content was determined using a commercial protein assay kit with BSA standards according to the manufacturer's instruction (Pierce, Rockford, Ill., USA).

Serum samples were thawed at room temperature and incubated with 5 volumes of Affi-Gel® Blue and incubated for 1 h or 16 h at 4° C. on a rotary platform. Samples were centrifuged at 2000 g for 10 min. The supernatants were recovered and aliquots (100 µl) were removed for the determination of total protein after correcting for dilution factors.

Affi-Gel® Blue Plus Affi-Gel® Protein A

Human serum samples were treated with the components of the Aurum™ serum protein mini-kit (Bio-Rad Laboratories, USA). This kit utilizes spin columns containing a mixture of Affi-Gel® Blue and Affi-Gel® Protein A to selectively bind and remove albumin and immunoglobulin. The Aurum™ matrix (Bio-Rad Laboratories, USA) in a Micro Bio-Spin Column was washed twice with 1 ml of binding buffer (20 mM phosphate buffer, pH 7.0) by centrifugation for 20 sec at 1000×g. Sixty µl of serum was added to 180 µl of binding buffer and mixed by vortexing. 200 µl was added to the Aurum™ matrix. Following incubation at room temperature for 15 min, 1 h, 5 h, or 16 h the column was centrifuged for 20 sec at 1000×g to collect the eluate. The column was washed with 200 µl of binding buffer and combined with the first eluate to form the depleted serum sample. The total protein concentration of the combined eluate was determined after taking the dilution factors into account. The eluate was stored at −80° C. until further analysis.

2 Dimensional Electrophoresis

First Dimension Separation:

Fifty µl of neat serum was diluted in sample preparation buffer and was incubated at 95° C. for 5 min. Fifteen µg of treated serum protein or diluted neat serum protein solubilization buffer was subjected to first-dimension separation as described in Example 6. Ready Strips were then stored at −80° C. until second dimension processing.

Second Dimension Separation:

Ready Strips from the first dimension separation were subjected to second-dimension separation as described for Example 7, except that 10% Tris-HCl Precast Criterion Gels (Bio-Rad Laboratories, USA) were used. The gels were analyzed using PDQuest version 6. The computer program identified protein spots from the digitalized images of the gel. Each serum sample was repeated three times, and variability between the experiments was assessed on three different gels.

The serum protein yields obtained using untreated and Affi-Gel® Blue or Aurum™ kit-treated specimens are summarized in Table 2. Both treatment methods removed 96-98% of total serum protein in 16 h, but with equal protein loading (~15 µg), there was no significant change in the total number of detectable protein spots by 2-DE analysis.

TABLE 2

Serum protein concentration and the number of protein spots obtained before and after treatment with Affi-Gel ® Blue or Aurum ™ kit

| Treatment | Total protein (mg/ml) | | | Total Number of Spots | | |
|---|---|---|---|---|---|---|
| | Gel 1 | Gel 2 | Gel 3 | Gel 1 | Gel 2 | Gel 3 |
| Untreated | 58.9 | 60.6 | 70.9 | 163 | 174 | 190 |
| Mean | | 63.46 ± 3.8 | | | 175 ± 7 | |
| Affi-Gel ® Blue | 2.05 | 2.26 | 2.7 | 210 | 222 | 232 |
| Mean | | 2.34 ± 0.33 | | | 220 ± 5 | |
| Aurum ™ kit | 0.8 | 0.83 | 1.26 | 142 | 151 | 160 |
| Mean | | 0.96 ± 0.26 | | | 151 ± 5 | |

Values are mean ± SEM of three different gels run on three different days.

As shown in FIG. 6, a SYPRO Ruby-stained 2-DE gel of serum samples revealed a typical 2-DE serum profile (FIG. 6a). The albumin smear at around 68 kDa was present in the untreated control sample, but was absent in the 16 h Affi-Gel® Blue and Aurum™ kit treated serum samples (FIGS. 6a, b and c).

Figure 7:
FIG. 7 is a depiction of the reference profile of all protein spots identified by 2-DE. (a) Protein spots enhanced by 5-fold after Affi-Gel® Blue treatment (in green) and (b) enhanced by 5-fold after Aurum™ kit treatment (in green).
Figure 7:

Removal of albumin resulted in a significant enhancement in the staining intensity of several protein spots, as summarized in Table 3 and illustrated in FIGS. 7a and 7b.

TABLE 3

Increased protein spot counts in Affi-Gel ® Blue treated serum as compared to untreated serum.

| Spots Increased | Number of Spot Counts |
|---|---|
| Two-fold | 53 ± 6 |
| Five-fold | 31 ± 5 |
| Ten-fold | 12 ± 3 |
| Twenty-fold | 6 ± 1 |

Values are mean ± SEM of six different serum samples.

Affi-Gel® Blue treatment resulted in the enhancement of 53 protein spots by 2-fold, 31 by 5-fold, 12 by 10-fold and 6 by 20-fold (FIG. 7a). In parallel, 16 h Aurum™ kit treatment resulted in 2, 5, 10 and 20-fold enhancement of 30, 13, 8 and 5 protein spots respectively, as shown in Table 4 and FIG. 7b.

TABLE 4

Increased protein spot counts in Aurum ™ kit treated serum as compared to untreated serum

| Spots Increased | Number of Spot Counts |
|---|---|
| Two-fold | 30 ± 6 |
| Five-fold | 13 ± 4 |
| Ten-fold | 8 ± 4 |
| Twenty-fold | 5 ± 2 |

Values are mean ± SEM of six different serum samples.

The pattern of enhanced visualization of protein spots with both treatment methods was similar, but more protein spots were revealed following Affi-Gel® Blue treatment.

Figure 8:
FIG. 8 is a depiction of the reference profile of all protein spots identified by 2-DE. (a) Profile of proteins unique to Affi-Gel® Blue treatment compared to untreated serum (in red), (b) Profile of proteins unique to Aurum™ kit treatment compared to untreated serum (in red). Results are representative of three independent experiments.
Figure 8:

Further analysis showed that 28 protein spots were found only after Affi-Gel® Blue treatment, and were not visualized in untreated serum (FIG. 8a). In contrast, only 2 protein spots were found after Aurum™ kit treatment, consistent with the loss of more protein with this treatment method (FIG. 8b).

These results suggest that Affi-Gel® Blue or Aurum™ kit treatment of human serum results in the removal of high abundant proteins such as albumin, thereby not only increasing the detection of low abundance proteins, but also allowing the detection of some otherwise undetectable proteins, which in the presence of albumin would have remained obscured.

Individual variations in the protein profile of the same serum samples prepared on three different days and repeated three times were investigated to eliminate confounding factors which might arise from sample handling. No substantial variation in the profile of protein spots from the same sample repeated on different days was detected (Table 2).

EXAMPLE 9

Time Course of Albumin Removal

Figure 9A:
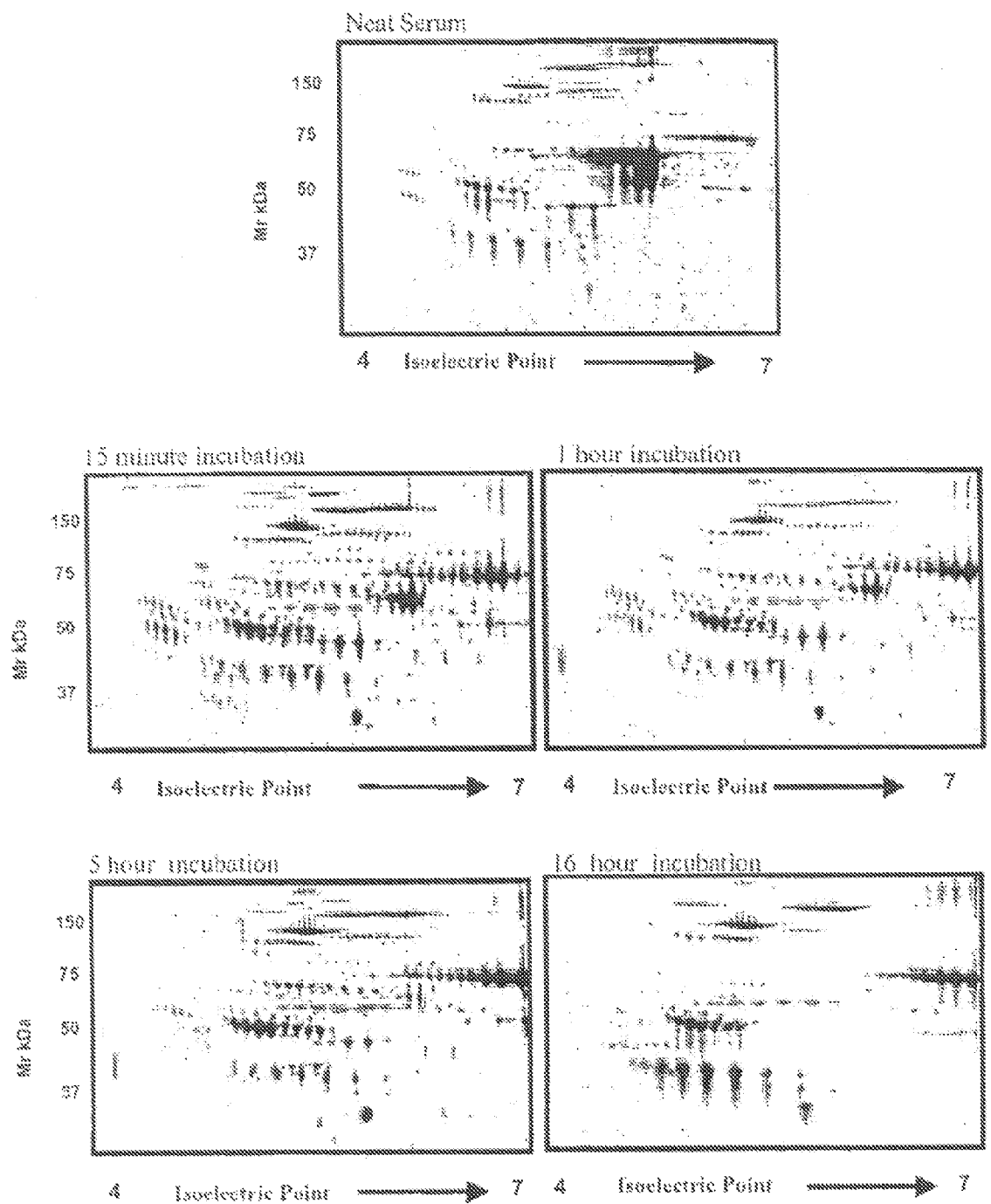
FIG. 9 shows time-dependent removal of albumin after treatment of human serum with Affi-Gel® Blue or Aurum™ kit. (a) Serum sample was treated with Aurum™ kit for 0 min (untreated serum), 15 min, 1 h, 5 h and 16 h. (b) Serum sample was treated with Affi-Gel® Blue for 0 min (untreated serum), 1 h and 16 h. 15 µg of protein was loaded on each gel.
Figure 9B:
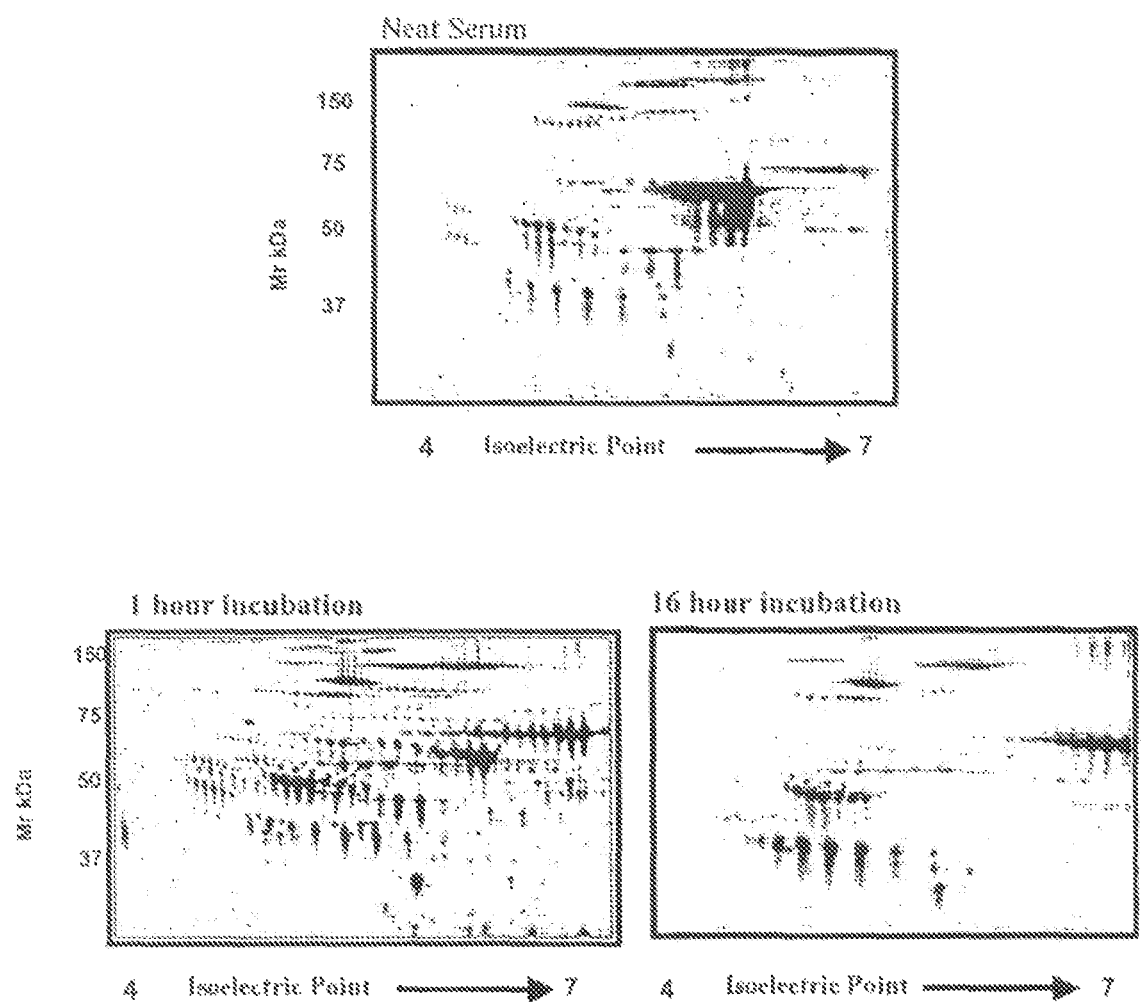

To determine if the removal of albumin by Affi-Gel® Blue or the Aurum™ kit removes protein spots other than albumin with increasing time, a time course study was performed. Human serum samples were treated with Affi-Gel® Blue for 1 and 16 h and with Aurum™ kit for 15 min, 1 h, 5 h and 16 h respectively. 15 µg of these samples was analyzed after resolving by 2-DE. Within 15 min of Aurum™ kit treatment there was a 98% loss of total serum protein, with an accompanying decrease in albumin staining and a two-fold increase in the number of protein spots. Within 1 h of Affi-Gel® Blue or Aurum™ kit treatment, significant depletion of albumin was achieved, with no significant loss of protein profile or number of protein spots. However, treatment with Affi-Gel® Blue or Aurum™ kit for 16 h resulted in the depletion of albumin, with an approximately 35% loss of total number of protein spots compared to 1 h treatment. These results are summarised in Tables 5 and 6, and illustrated in FIG. 9.

TABLE 5

Time course of serum protein concentration and number of protein spots following Aurum ™ kit treatment

| Treatment | Protein Concentration (mg/ml) | Reduction in Protein Concentration (%) | Number of Spots |
|---|---|---|---|
| Untreated | 62.3 | 0 | 174 |
| 15 min | 1.45 | 98 | 365 |
| 1 h | 1.02 | 99 | 337 |

TABLE 5-continued

Time course of serum protein concentration and number of protein spots following Aurum ™ kit treatment

| Treatment | Protein Concentration (mg/ml) | Reduction in Protein Concentration (%) | Number of Spots |
|---|---|---|---|
| 5 h | 1.02 | 99 | 287 |
| 16 h | 0.92 | 99 | 221 |

TABLE 6

Time course of serum protein concentration and number of protein spots following Affi-Gel ® Blue treatment

| Treatment | Protein Concentration (mg/ml) | Reduction in Protein Concentration (%) | Number of Spots |
|---|---|---|---|
| Untreated | 62.3 | 0 | 174 |
| 1 h | 2.65 | 96 | 330 |
| 16 h | 2.20 | 96 | 220 |

These observations suggest that although 16 h exposure of human serum to Affi-Gel® Blue or Aurum™ kit can result in significant depletion of albumin and consequent enhancement of several low-abundance proteins, it is also associated with non-specific removal of serum protein other than albumin.

Our results demonstrate that Affi-Gel® Blue and Aurum™ kit treatment results in the removal of highly abundant albumin, and simultaneous enhancement in the detection of several other proteins. Within 16 h both treatment methods removed 96-98% of total protein content of the serum, but there were no significant differences in the total number of protein spots analyzed after 2-DE analysis. We have also shown that Affi-Gel® Blue and Aurum™ kit treatment removes high abundant albumin and enhances the staining intensity of different spots by several-fold. In addition, with equal protein loading, 28 and 2 unique spots respectively were detected by Affi-Gel® Blue and Aurum™ kit treatment compared to neat serum. These spots remained obscured in the neat untreated serum samples.

Aurum™ kit treatment results in a greater depletion of protein, as its Protein A component also removes immunoglobulins. The serum pattern of IgG (heavy chain) is apparent over a pI range of 6.5-8.3. As this range falls in the borderline of the pI range used in this study, a less defined pattern of IgG heavy chain was evident on the gels. Sixteen h treatment with Affi-Gel® Blue or the Aurum™ kit resulted in the removal of proteins other than albumin. Affi-Gel® Blue and the Aurum™ kit bind albumin with high affinity, but other proteins can also bind to the planar ring structure of the Cibracon Blue 3G dye, through a complex combination of electrostatic, hydrophobic and hydrogen bonding interactions. Hence non-specific removal of protein other than albumin after 16 h of treatment with Affi-Gel® Blue or the Aurum™ kit is not surprising. However, by using this protein depletion step for only 1 h, significant depletion of albumin can be achieved with minimal non-specific protein removal. While both Affi-Gel® Blue and the Aurum™ kit are effective reagents for the depletion of highly abundant albumin, greater sensitivity in protein profiling without any significant loss of potential serum biomarker can be achieved only if the samples are exposed to the reagents for a period of 1 h. This approach can generate a pattern of protein profiles independent of the identity of individual proteins, and can be used as a discriminator of a particular disease state.

It will be evident that a protein A absorption step using the Aurum™ kit or another protein A affinity support can be combined with the immunodepletion step described herein, as an alternative to Affi-Gel® blue.

Our data suggest that by using the method of the invention for sample processing before 2-DE or other methods of protein analysis, one can increase the likelihood of discovery of novel biomarkers of high sensitivity and specificity.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention claimed is:

1. A method of depleting a high abundance molecule from a biological sample, comprising the steps of:
    a) subjecting the sample to affinity depletion using an affinity support with high affinity for the high abundance molecule; and
    b) immunodepleting the sample using an affinity support coupled to a chicken IgY antibody, wherein the chicken IgY antibody is a second generation or higher antibody raised against whole blood, serum or plasma or against whole blood, serum or plasma that has already been subjected to at least one round of affinity depletion or immunodepletion, and wherein the chicken IgY antibody binds a plurality of different high abundance molecules.

2. The method of claim 1, in which the IgY chicken antibody is a second antibody raised against whole blood, serum or plasma or against whole blood, serum or plasma that has already been subjected to one round of affinity depletion or immunodepletion.

3. A method of depleting a high abundance molecule from a biological sample, comprising the steps of:
    a) subjecting the sample to affinity depletion using an affinity support with high affinity for the high abundance molecule; and
    b) immunodepleting the sample using an affinity support coupled to a chicken IgY antibody, wherein the chicken IgY antibody is a second generation or higher antibody raised against whole blood, serum or plasma, or against whole blood, serum or plasma that has already been subjected to at least one round of affinity depletion or immunodepletion, and wherein the chicken IgY antibody binds a plurality of different high abundance molecules.

4. The method of claim 1, wherein the whole blood, serum or plasma is of human origin.

5. The method of claim 1, in which step (a) is performed before step (b).

6. The method of claim 1, in which the high abundance molecule is a protein.

7. The method of claim 6, in which the protein is albumin or immunoglobulin.

8. The method of claim 1, in which the biological sample is conditioned medium from a cell or tissue culture, or is a tissue or cell extract.

9. The method of claim 1, in which the affinity support used in step (a) is a dye affinity chromatography resin.

10. The method of claim 9, in which the dye is a chlorotriazine compound.

11. The method of claim 10, in which the affinity support is a Cibacron blue F3GA affinity support.

12. The method of claim 1, in which the affinity support used in step (a) comprises a magnetic bead.

13. A method of separation or analysis of a low abundance molecule in a biological sample, comprising the step of depleting at least one high abundance molecule from the sample by the method of claim 1, prior to subjecting the sample to one or more separation or analytical steps for the separation or analysis of the low abundance molecule.

14. A method of identifying the expression of a low abundance molecule in a mammal, comprising the step of depleting at least one high abundance molecule from a biological sample from the mammal by the method of claim 1, prior to subjecting the sample one or more analytical steps to detect the expression of the low abundance molecule.

15. A method of claim 14, in which a change in the expression of the low abundance molecule is detected.

\* \* \* \* \*